(12) United States Patent
Feke

(10) Patent No.: US 8,039,788 B2
(45) Date of Patent: Oct. 18, 2011

(54) IMAGING TARGET FOR TESTING QUALITY OF MULTIPLE-MAGNIFICATION FOCUS AND IMAGE CO-REGISTRATION

(75) Inventor: Gilbert Feke, Glastonbury, CT (US)

(73) Assignee: Carestream Health, Inc., Rochester, NY (US)

( * ) Notice: Subject to any disclaimer, the term of this patent is extended or adjusted under 35 U.S.C. 154(b) by 621 days.

(21) Appl. No.: 12/195,452

(22) Filed: Aug. 21, 2008

(65) Prior Publication Data

US 2009/0067582 A1 Mar. 12, 2009

Related U.S. Application Data

(60) Provisional application No. 60/970,564, filed on Sep. 7, 2007, provisional application No. 61/024,621, filed on Jan. 30, 2008.

(51) Int. Cl.
*G01D 18/00* (2006.01)
*G12B 13/00* (2006.01)

(52) U.S. Cl. .................................. 250/252.1; 378/207

(58) Field of Classification Search ............... 250/252.1; 378/207
See application file for complete search history.

(56) References Cited

U.S. PATENT DOCUMENTS

| | | | |
|---|---|---|---|
| 4,814,889 | A | 3/1989 | Covey |
| 5,651,046 | A | 7/1997 | Floyd et al. |
| 5,768,443 | A | 6/1998 | Michael et al. |
| 6,231,231 | B1 | 5/2001 | Farrokhnia et al. |
| 6,409,383 | B1 | 6/2002 | Wang et al. |
| 2008/0012006 | A1 * | 1/2008 | Bailey et al. .................... 257/40 |

OTHER PUBLICATIONS

Commonly assigned U.S. Appl. No. 61/024,621, filed Jan. 8, 2008, Feke et al., titled: Apparatus and Method for Multi-Modal Imaging.

* cited by examiner

*Primary Examiner* — David Porta
*Assistant Examiner* — Carolyn Igyarto

(57) ABSTRACT

An imaging target, suited for use in multi-modal imaging systems, includes test patterns for testing quality of both focus and co-registration for multiple magnifications and multiple modalities of operation of a multimodal imaging system.

16 Claims, 6 Drawing Sheets

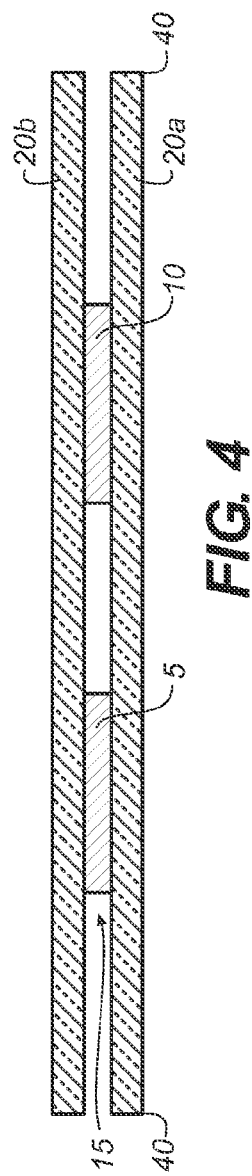

IMAGING TARGET FOR TESTING QUALITY OF MULTIPLE-MAGNIFICATION FOCUS AND IMAGE CO-REGISTRATION

CROSS REFERENCE TO RELATED APPLICATIONS

Priority is claimed from commonly assigned, copending provisional (a) U.S. Patent Application Ser. No. 60/970,564 filed Sep. 7, 2007 by Gilbert Feke entitled SELF-ALIGNING MULTIMODAL MULTIPLE-MAGNIFICATION FOCUS AND CO-REGISTRATION TEST PATTERN TARGET; and (b) U.S. Patent Application Ser. No. 61/024,621 filed Jan. 30, 2008 by Feke et al. entitled APPARATUS AND METHOD FOR MULTI-MODAL IMAGING.

FIELD OF THE INVENTION

The invention relates generally to the field of imaging. Patterns for testing the quality of both focus and co-registration for multiple magnifications and multiple modalities of operation are combined within a single imaging target that is particularly useful for a multimodal imaging system.

BACKGROUND OF THE INVENTION

In the field of multimodal imaging a single imaging station may be employed to image specimens using multiple imaging modalities. In a multimodal imaging system of the type disclosed in commonly assigned, copending (a) regular U.S. patent application Ser. No. 11/221,530 filed Sep. 8, 2005 by Vizard et al. entitled "APPARATUS AND METHOD FOR MULTI-MODAL IMAGING" and (b) Provisional Application Ser. No. 61/024,621, previously mentioned, the disclosures of both of which are incorporated herein by reference, a specimen to be imaged may be illuminated by optical back-illumination, optical front-illumination or X-ray back-illumination. The imaging modalities may include bright-field optical imaging at various wavelengths, dark field fluorescence optical imaging at various wavelengths, and radiographic imaging at various energies. There is a need for a simple way for combining, in a single imaging target, patterns for testing quality of both focus and co-registration for multiple magnifications and multiple modalities of operation of such multimodal imaging systems.

SUMMARY OF THE INVENTION

An imaging target according to an embodiment of the invention is suited for use in a multimodal imaging system. The target may comprise an optically clear, X-ray transparent substrate; at least one first pattern formed on the substrate for testing quality of image focus of one or more modalities of operation of the imaging system for a range of magnifications and illumination wavelengths; and at least one second pattern formed on the substrate for testing quality of image co-registration of one or more modalities of operation of the imaging system for a range of magnifications and illumination wavelengths. The first and second patterns may be formed from optically reflective, X-ray opaque material. A second optically clear, X-ray transparent substrate may be included on an opposite side of the first and second patterns from the first substrate, the second substrate being coated with an optically white, X-ray transparent material opposite at least one of the patterns. In another embodiment, the first and second patterns may be formed on a first side of the substrate and an optically white, X-ray transparent coating may be formed on a second side of the substrate opposite to at least one of the patterns.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures.

FIG. 4 shows a cross sectional view of the imaging target, taken along line 4-4 of FIG. 1.

DETAILED DESCRIPTION OF THE INVENTION

The present invention concerns a device with a target design, which provides a simple solution and method for combining, in a single imaging target, patterns for testing the quality of both focus and image co-registration for multiple magnifications and multiple modalities of operation of a multimodal imaging system. The imaging target according to the invention is self-aligning in the sense that it includes features such as alignment marks that can be registered with features of an associated imaging system, thus aligning the target to the imaging system. The imaging target according to the invention is useful in a multimodal imaging system that can image objects using bright field, dark field and X-ray imaging modes. Regarding such an imaging system, reference is made to previously mentioned regular U.S. patent application Ser. No. 11/221,530 and provisional U.S. Patent Application Ser. No. 61/024,621. By using a single imaging target or device 1 having a target design 2 as shown in FIGS. 1 to 6, sufficient imaging contrast is achieved so that one imaging target can be used to test both focus and image co-registration of multimodal imaging means such as bright-field optical images at various illumination wavelengths, fluorescence optical images at various illumination wavelengths, and radiographic images at various energies.

Figure 1:
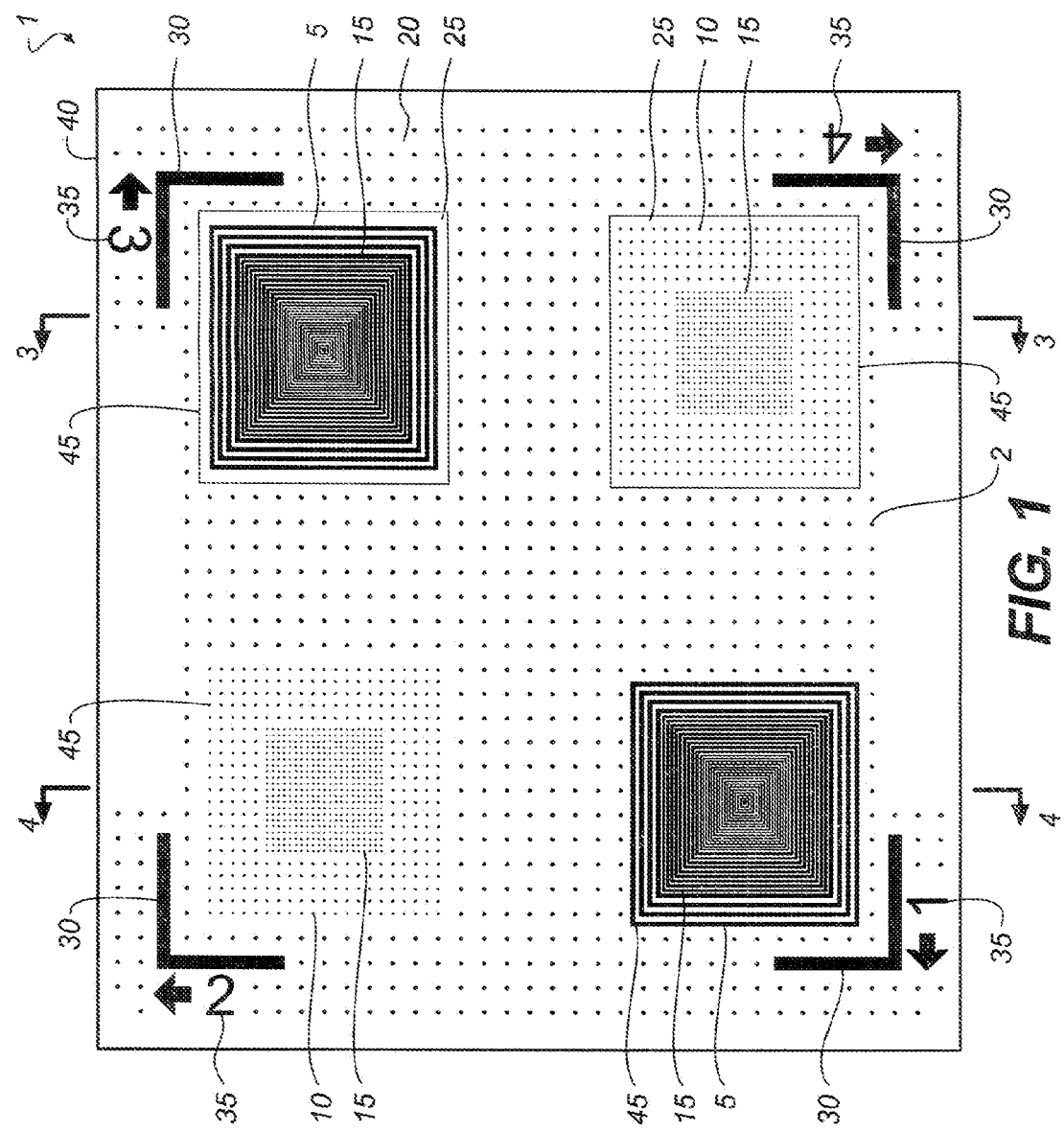
FIG. 1 is a plan view of the front side an imaging target made in accordance with the present invention.
Figure 2:
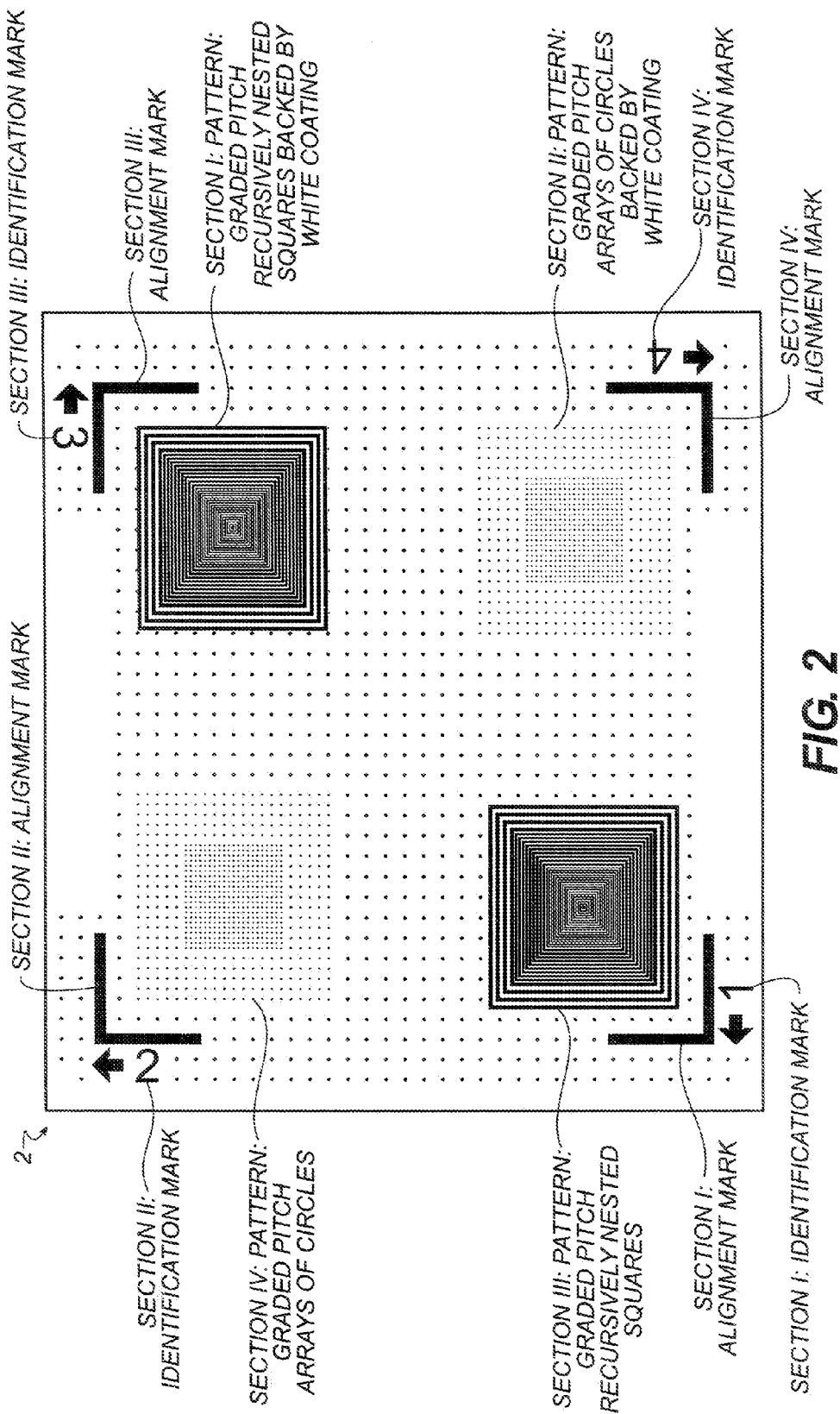
FIG. 2 is a plan view of the front side illustrating in further detail the four sections of target patterns shown in FIG. 1.

Referring to FIGS. 1 to 4, one embodiment of the invention includes a device 1 comprising a target design 2 having one or more sections I, II, III, and IV. Each target design comprises a plurality of layers 15, 20a, 20b and, in sections I and II, layer 25. The target designs further include patterns 5 for testing image focus and 10 for testing image co-registration. In each section patterns are formed on an optically clear, X-ray transparent substrate using known techniques to pattern an optically reflective, X-ray opaque material such as chemical etching of a copper film or screen printing of a silver ink. So, in the areas where the patterned material is present, imaging contrast is provided, with respect to the areas of device 1 where patterned material is not present, for at least one, more preferably more than one, and most preferably all of the modalities of operation of the imaging system. In areas of the device surrounding patterns 5 and 10, a background grid pattern of small dots or circles is applied using the same material. The array of dots or circles is useful for testing low magnification configurations of the imaging system. In one actual device as seen in FIGS. 1 and 2, which is useful within a magnification range of at least 0.075 to 0.15 for a system including a square 4 megapixel sensor having 0.8 inch diagonal dimension, these dots are 0.016 inch circles in a 37 by 37 array set at 0.145 inch pitch, with rectangular open spaces for patterns 5 and 10.

Patterns 5 comprise features useful for testing the quality of image focus of at least one, more preferably more than one, and most preferably all of the modalities of operation of the imaging system for a range of magnifications of the imaging system. Patterns 10 are useful for testing the quality of image co-registration among various illumination wavelengths and/or modalities of at least one, more preferably more than one, and most preferably all of the modalities of operation of the imaging system for a range of magnifications of the imaging system.

Referring still to FIGS. 1 to 4, device 1 includes a plurality of alignment features. These features may include patterned alignment features, such as right-angle alignment marks 30 applied at each corner of the device or the physical, rectangular boundary 40 of device 1, or both. The device may have any convenient shape at its boundary. In the illustrated embodiment, patterns 5 and 10 are applied at opposite corners of a device having a rectangular boundary 40. As illustrated, each of patterns 5, 10 may have an essentially rectangular boundary 45. Each set of alignment marks 30 corresponds either to a diagonally opposite pattern of recursively nested geometric figures such as rectangles or squares in pattern 5 or a diagonally opposite graded pitch array of circles in pattern 10. Alignment marks 30, in use, will be registered to physical features of the imaging system. Such as marks or features may be provided at the focal plane of the system, such as on a system platen or a support for an object to be imaged, not illustrated. Each of alignment marks 30 is positioned with respect to a diagonally opposite one of patterns 5, 10 in the corresponding section I to IV. When an alignment mark 30 has been registered to a feature of the imaging system, the center of a selected pattern diagonally opposite the registered alignment mark will be aligned to the center of the field of view of the imaging system. Target design 2 also may include a plurality of identification numerals or marks 35, each mark 35 corresponding to one of sections I to IV and providing information regarding the identity of its respective section.

Within each of boundaries 45, target design 2 comprises a layer 15 with patterned material forming patterns 5, 10 and the background grid pattern of dots or circles previously mentioned, on an optically clear, X-ray transparent substrate 20a. The patterns 5, 10 may be formed from a suitable X-ray opaque metallic material such as copper film or silver ink. The substrate 20a may be formed from optically clear polyester such as Mylar. The patterns formed in layer 15 and substrate 20a provide sufficient imaging contrast so that the patterns of sections I to IV can be used as appropriate to test quality of focus and/or co-registration of bright-field optical images at various illumination wavelengths, fluorescence optical images at various illumination wavelengths, and/or radiographic images at various energies. Test results for quality of focus and/or co-registration of bright-field optical images also may be applied to the dark-field optical imaging mode. A cover substrate 20b of optically clear polyester may be included on opposite side of material 15 from substrate 20a.

Figure 3:
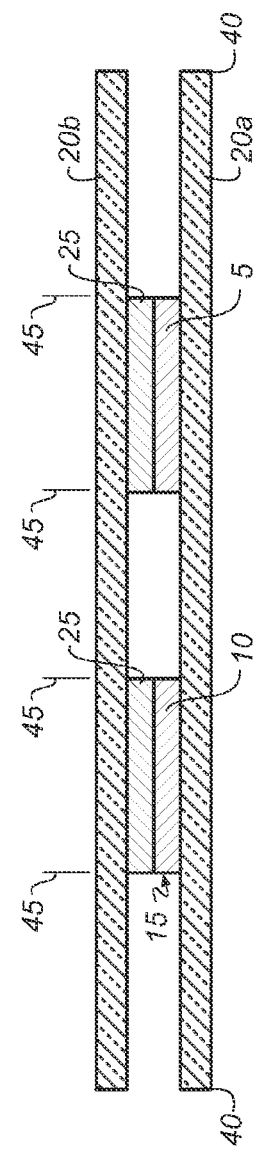
FIG. 3 shows a cross sectional view of the imaging target, taken along line 3-3 of FIG. 1.

As shown in FIG. 3, in sections I and II, patterns 5, 10 are covered by a layer 25 formed on a portion of polyester substrate 20b coated with an optically white, X-ray transparent material. When visible light is passed through from behind the target in a bright-field imaging mode, layer 25 diffuses the back-lighting, thus eliminating the need for any separate external diffuser. Sections I and II also may be used for X-ray imaging mode. As shown in FIG. 3, patterns 5 and 10 include two layers, a portion of layer 15 including a patterned material on substrate 20a; and a layer comprising layer 25 overlying the patterned material. The patterned material, layer 25 and substrate 20a provide sufficient imaging contrast so that sections I and II can be used as appropriate to test quality of focus and/or co-registration of bright-field optical images at various illumination wavelengths, fluorescence optical images at various illumination wavelengths, and/or radiographic images at various energies. As shown in FIG. 4, layer 25 is not provided for patterns 5, 20 in Sections III and IV. Sections III and IV may be used for front-lighting and X-ray imaging mode.

Figure 5B:
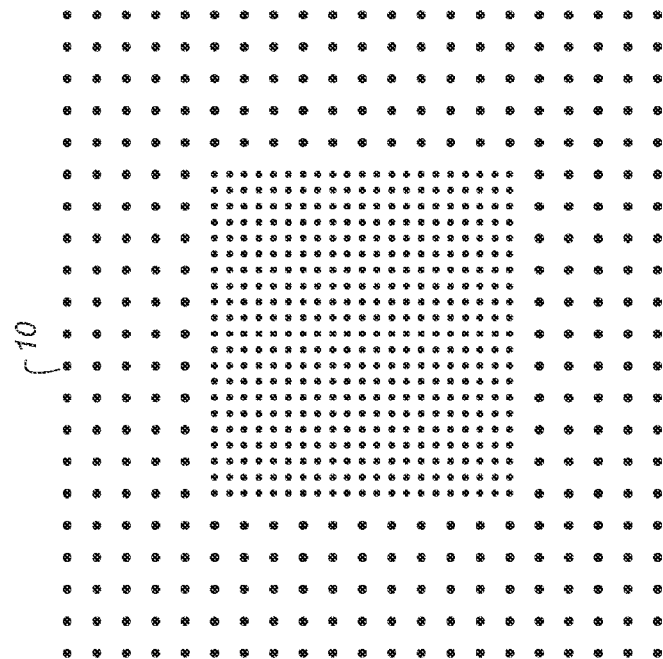
FIGS. 5A and 5B are enlarged schematic plan views of the graded-pitch nested-square pattern and the graded-pitch array of circles pattern in accordance with the present invention.
Figure 5A:
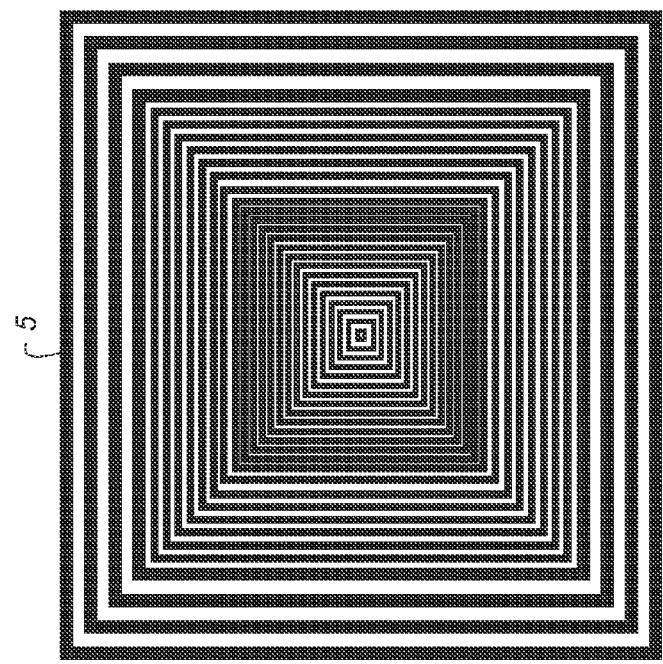

In sections I and III, pattern 5 comprises recursively nested geometric shapes, such as rectangles or the illustrated squares, whereby the center of the pattern may be aligned to the center of the field of view of the imaging system by the physical registration of a corresponding set of alignment features of device 1 to a set of physical features of the imaging system, as previously discussed. The nesting pitch of the geometric shapes is graded to higher pitch and smaller size toward the center of the pattern to provide sufficient pattern content to test imaging system focus quality for multiple magnifications of the imaging system. The line width is equal to half the pitch, as is the spacing between lines. In one actual device as seen in FIG. 5A, which is useful within a magnification range of at least 0.075 to 0.75 for a system including a square 4 megapixel sensor having 0.8 inch diagonal dimension, the pitches are 0.006 inch for 16 nest levels, 0.011 inch for 7 nest levels, 0.016 inch for 8 nest levels, 0.032 inch for eight nest levels and 0.063 inch for 4 nest levels.

In sections II and IV, a pattern 10 comprises a graded pitch array of a shape, such as the illustrated tiny circles, whereby the center of the pattern may be aligned to the center of the field of view of the imaging system by the physical registration of a corresponding set of alignment features of device 1 to a set of physical features of the imaging system, as previously discussed. The graded pitch arrays range in pitch and the circular shapes range in size, whereby the array pitch and shape size are graded to higher pitch and smaller size toward the center of the pattern to provide sufficient pattern content to test quality of co-registration for multiple magnifications of the imaging system. In one actual device as seen in FIG. 5B, which is useful within a magnification range of at least 0.15 to 0.75 for a system including a square 4 megapixel sensor having 0.8 inch diagonal dimension, going out from the center of the array, the pitches are 0.037 inch for a 21 by 21 array of 0.004 inch diameter circles; and 0.071 inch for a 21 by 21 array of 0.008 inch diameter circles.

Figure 6:
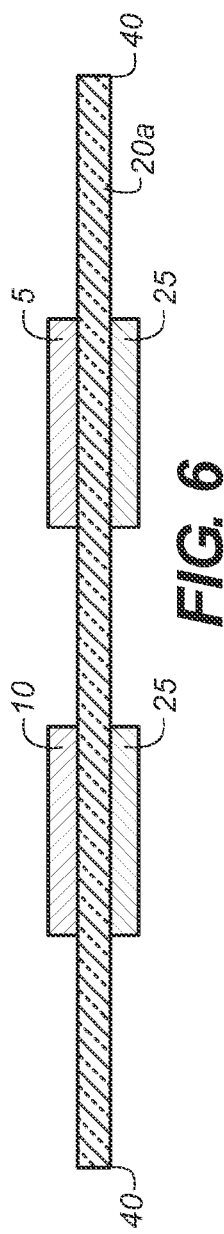
FIG. 6 is a side view of another embodiment of the imaging target in which a single substrate is used.

FIG. 6 shows a side view of an imaging target in which a single polyester substrate 20 has patterns 5 and 10 formed on one side and white coating layers 25 formed on the opposite side, for Sections I and II. Sections III and IV may be formed on either side of substrate 20. This target is somewhat easier to manufacture than that of FIGS. 1 to 4, though its lack of a second protective polyester layer may make it more vulnerable to scratches and wear.

The method for use of the target involves steps of: placing the target in the multimodal imaging system; using identifying marks 35, identifying the section(s) of the target to be used for multimodal focus quality and/or co-registration quality testing; physically registering the alignment features of the device 1, such as patterned alignment marks 30 and/or the physical boundary 40 of the device, to the corresponding physical features of the multimodal imaging system so that the center of the corresponding section is aligned to the center of the field of view of the multimodal imaging system; setting the magnification of interest of the multimodal imaging system; setting the illumination wavelength or energy for the modality of interest; acquiring one or more images of the target; and evaluating the focus quality and/or co-registration quality of the acquired images. The evaluations of focus quality and co-registration quality may be performed using software tools familiar to those skilled in the art.

The invention has been described with reference to a preferred embodiment, however, it will be appreciated that variations and modifications can be effected by a person of ordinary skill in the art without departing from the scope of the invention.

PARTS LIST

1 Imaging target or device
2 Target design
5 Graded pitch recursively nested square pattern
10 Graded pitch array of circles pattern
15 Patterned material layer
20a, 20b Optically clear polyester layer substrate
25 White coating layer
30 Alignment mark
35 Identification mark
40 Identification boundary of device 1
45 Physical boundary of target pattern 5 or 10

What is claimed is:

1. An imaging target for use in a multimodal imaging system, the target comprising:
    an optically clear, X-ray transparent substrate;
    at least one first pattern formed on the substrate for testing quality of image focus of one or more modalities of operation of the imaging system for a range of magnifications and illumination wavelengths; and
    at least one second pattern formed on the substrate for testing quality of image co-registration of one or more modalities of operation of the imaging system for a range of magnifications and illumination wavelengths, the first and second patterns being formed from optically reflective, X-ray opaque material.

2. The imaging target according to claim 1, wherein each of the first and second patterns comprises:
    at least one layer of the material, the material forming a pattern which provides imaging contrast for one or more of the modalities of operation of an imaging system, with respect to the areas where the patterned material is absent; the pattern comprising features used for testing at least one of the quality of image focus or the quality of image co-registration.

3. The imaging target according to claim 2, further comprising:
    at least one alignment feature positioned corresponding to at least one of the first and second patterns for registering the imaging target to a feature of the imaging system to locate the at least one pattern in a field of view of the imaging system; and
    at least one identification mark corresponding to at least one of the first and second patterns for providing information regarding the identity of the pattern.

4. The imaging target according to claim 3 wherein at least one of the patterns includes:
    a pattern of a recursively nested geometric shapes, the center of the pattern being suited to be aligned to a center of the field of view of the imaging system by the registration of the at least one alignment feature to a feature of the imaging system, and
    the pattern of geometric shapes having a nesting pitch graded to lower pitch toward the center of the pattern to provide sufficient pattern content to test quality of focus for multiple magnifications of the imaging system.

5. The imaging target according to claim 4, wherein the geometric shape is rectangular.

6. The imaging target according to claim 3 wherein at least one of the patterns includes:
    a pattern of an array of a geometric shape, the center of the pattern of an array being suited to be aligned to a center of the field of view of the imaging system by the registration of at least one alignment feature to a feature of the imaging system, and
    the array pitch of the geometric shape being graded to lower pitch toward the center of the pattern to provide sufficient pattern content to test imaging system co-registration quality for multiple magnifications of the imaging system.

7. The imaging target according to claim 6, wherein the geometric shape is circular.

8. The imaging target according to claim 1 wherein the modalities of operation of the imaging system include bright-field optical imaging at various wavelengths, fluorescence optical imaging at various wavelengths, and radiographic imaging at various energies.

9. The imaging target according to claim 1 wherein the first and second patterns are formed from a copper film.

10. The imaging target according to claim 1 wherein the first and second patterns are formed from silver ink.

11. The imaging target according to claim 1 wherein the substrate is optically clear polyester.

12. The imaging target according to claim 1, wherein the first and second patterns are formed on a first side of the substrate, further comprising an optically white, X-ray transparent coating formed on a second side of the substrate opposite to at least one of the patterns.

13. An imaging target for use in a multimodal imaging system, the target comprising:
    a first optically clear, X-ray transparent substrate;
    a pattern of X-ray opaque metallic material formed on the substrate for testing quality of image focus or image co-registration; and
    a second optically clear, X-ray transparent substrate on an opposite side of the pattern of X-ray opaque metallic material from the first substrate, the second substrate being coated opposite the pattern with an optically white, X-ray transparent coating opposite to the pattern,
    whereby the first and second substrates and the pattern provide sufficient imaging contrast to test quality of focus or quality of co-registration, or both, of at least one or more modalities of operation of the imaging system.

14. The imaging target according to claim 13, wherein the X-ray opaque metallic material is copper.

15. The imaging target according to claim 13, wherein the X-ray opaque metallic material is silver ink.

16. The imaging target according to claim 13 wherein the modalities of operation are bright-field optical imaging at various wavelengths, fluorescence optical imaging at various wavelengths, and radiographic imaging at various energies.

* * * * *